(12) United States Patent
Kösslinger et al.

(10) Patent No.: US 6,196,059 B1
(45) Date of Patent: *Mar. 6, 2001

(54) PIEZOELECTRIC RESONATOR, PROCESS FOR THE FABRICATION THEREOF INCLUDING ITS USE AS A SENSOR ELEMENT FOR THE DETERMINATION OF THE CONCENTRATION OF A SUBSTANCE CONTAINED IN A LIQUID AND/OR FOR THE DETERMINATION OF THE PHYSICAL PROPERTIES OF THE LIQUID

(75) Inventors: Conrad Kösslinger; Erich Uttenthaler, both of München; Andreas Nitsch, Finning; Thomas Härle, Stadtbergen, all of (DE)

(73) Assignee: Fraunhofer Gesellschaft zur Forderung der angewandten Forschung e.V., Munich (DE)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/132,617

(22) Filed: Aug. 11, 1998

(30) Foreign Application Priority Data

Aug. 11, 1997 (DE) .............................. 197 34 406

(51) Int. Cl.[7] .......................... G01N 27/00; G01N 27/26; H01L 41/08; G01H 01/00

(52) U.S. Cl. .................................. 073/61.49; 073/24.06; 073/61.45; 073/61.75; 073/592; 310/364; 310/322

(58) Field of Search .................................. 310/363–366, 310/321, 322, 324, 365, 24.06; 73/61.49, 61.45, 61.75, 592

(56) References Cited

U.S. PATENT DOCUMENTS 2,385,896 * 10/1945 Beckerath ........................ 310/365 X (List continued on next page.)

FOREIGN PATENT DOCUMENTS

0132187 * 10/1979 (JP) ...................................... 310/364
0128809 * 6/1988 (JP) ...................................... 310/364

Primary Examiner—Hezron Williams
Assistant Examiner—David J. Wiggins
(74) Attorney, Agent, or Firm—Antonelli, Terry, Stout & Kraus, LLP.

(57) ABSTRACT

Disclosed is a piezoelectric resonator, a process for the fabrication thereof and its use as a sensor element, which implemented in a through-flow cell, is integratable in a measurement system for the determination of the concentration of a substance contained in a liquid and/or for the determination of the physical properties of the liquid. The piezoelectric resonator is designed plane and is provided on its surface with electric contact areas for an electrode and a counter electrode, which is connectable to a signal source as well as to a measurement device. For measuring, the piezoelectric resonator is brought into contact with the to-be-examined liquid on one side, with the resonator responding to the accumulation of the mass of the to-be-detected substance or to a change in the physical properties of the liquid by changing its resonance frequency and/or oscillation amplitude.

The present invention is distinguished by the fact that the piezoelectric resonator is provided with contact electrode areas which is contactable from one single side of the resonator. The resonator is the heart piece of a sensor element, which is integrated in a through-flow cell. The through-flow cell us insertable module-like in a measurement arrangement for determining the concentration of a substance contained in a liquid and/or determining the physical properties of the liquid.

30 Claims, 4 Drawing Sheets

U.S. PATENT DOCUMENTS

| | | | | |
|---|---|---|---|---|
| 3,307,052 | * | 2/1967 | Neilson et al. | 310/366 X |
| 3,495,105 | * | 2/1970 | Shimano | 310/366 |
| 3,727,084 | * | 4/1973 | Epstein | 310/364 X |
| 4,365,515 | * | 12/1982 | Abts | 310/334 X |
| 4,604,543 | * | 8/1986 | Umemura et al. | 310/366 X |
| 4,658,650 | * | 4/1987 | Yorinaga et al. | 73/654 |
| 4,728,844 | * | 3/1988 | Wilson et al. | 310/327 |
| 5,130,257 | * | 7/1992 | Baer et al. | 436/151 |
| 5,334,303 | * | 8/1994 | Muramatsu et al. | 310/364 X |
| 5,507,178 | * | 4/1996 | Dam | 73/61.49 |
| 5,616,872 | * | 4/1997 | O'Brien | 73/865.5 |
| 5,705,399 | * | 1/1998 | Larue | 436/501 |
| 5,723,773 | * | 3/1998 | Bryan | 73/61.75 |
| 5,757,104 | * | 5/1998 | Getman et al. | 310/317 |
| 5,789,846 | * | 8/1998 | Brown | 310/366 |
| 5,817,921 | * | 10/1998 | Tom et al. | 73/24.01 |
| 5,852,229 | * | 12/1998 | Josse et al. | 73/24.06 |
| 5,866,798 | * | 2/1999 | Schonfeld et al. | 73/24.06 |
| 5,869,748 | * | 2/1999 | Stevenson et al. | 73/53.01 |
| 5,920,007 | * | 7/1999 | Hirota et al. | 73/61.75 |

* cited by examiner

PIEZOELECTRIC RESONATOR, PROCESS FOR THE FABRICATION THEREOF INCLUDING ITS USE AS A SENSOR ELEMENT FOR THE DETERMINATION OF THE CONCENTRATION OF A SUBSTANCE CONTAINED IN A LIQUID AND/OR FOR THE DETERMINATION OF THE PHYSICAL PROPERTIES OF THE LIQUID

BACKGROUND OF THE INVENTION

1. Field of the Invention

The present invention relates to a piezoelectric resonator, a process for the fabrication thereof, its use as a sensor element, which, implemented in a through-flow cell, is integrable in a measurement system for the determination of the concentration of a substance contained in a liquid and/or for the determination of the physical properties of the liquid. The piezoelectric resonator is designed plane and is provided, on its surface, with electric contact areas for electrodes and counter electrodes, which is connectable to a signal source as well as to a measurement device. For measuring, the piezoelectric resonator is brought into contact with the to-be-examined liquid on one side, and the resonator responds to the accumulation of the mass of the to-be-detected substance or to a change in the physical properties of the liquid by altering its resonance frequency and/or oscillation amplitude.

2. Description of the Prior Art

Usually, piezoelectric resonators are provided with small oscillator quartz plates, which provide conductive contact areas for the integration and the electric contacting to an electric oscillation circuit, via which connecting an alternating voltage, which resonates typically for the small plates, can be applied to the small oscillator quartz plates. However, due to the structure of the small plates, which can meanwhile be fabricated in a filigree manner, the resonating behavior of the resonator may be impaired, i.e. by mechanical tension in the small plates caused by the holding carriers or by contacting with electric lines.

An example of a small oscillator quartz plate that is fixed in a holding carrier is described in DE 34 46 612 A1. The small oscillator quartz plate 8 is provided with electrodes 301 deposited on its surface and is spatially fixed between two holding clamps 201 and electrically contacted. What is disadvantageous in this setup, however, is that even with the least exerted force, which can act on the two parts 7 which are spaced apart, can generate mechanical tension in the small plate 8 glued between parts 7, thereby influencing the resonance behavior of small plate 8.

Among other things, piezoelectric resonators are used as active sensor elements, for example, for detecting a substance in a medium, for instance, for measuring the concentration of the substance in a liquid. In addition to the aforementioned problem of ensuring tension-free holding of a small oscillator quartz plate, when working with liquids, the oscillator quartz to be electrically contacted has also to be insulated liquid-tight against the to-be-examined liquid in order to prevent electric short circuits. Such a sensor is described in DE 40 13 665. This known sensor provides a small oscillator quartz plate 4, which is clamped on both sides between two silicon seals and, in addition, is contacted to conductive adhesive substances. However, the use of conductive adhesives has the consequence that the electric contact cannot be disconnected, which, for instance, makes replacing the small oscillator quartz plate impossible or at least requires great manual skill. Moreover, the silicon seals surrounding the small oscillator plates from all sides have to be made with great precision in order to prevent deformations in the small plate.

A similar setup for measuring the concentration of certain substances dissolved in a liquid using a small oscillator quartz plate is described in the article by W. Stöckl and R. Schumacher, "In Situ Microweighing at the Junction Metal/Electrode", Berichte der Bunsengesellschaft physikalische Chemie 91 (1987, pp. 345–349. The small oscillator quartz plate is electrically contacted on both sides at its edge areas. By means of a suited liquid sealing at one side of the small oscillator quartz plate, the to-be-examined liquid comes into surface contact with the small plate so that the resonance behavior of the small plate alters accordingly and measuring can be conducted in the known manner. Similarly operating sensors using piezoelectric resonators for immunoanalysis are known from the articles by K. Davis, T. Leary, "Continuous Liquid-Phase Piezoelectric Biosensor of Immunoassays", Anal. Chem. 1989, No. 61, pp. 1227–1230 and by M. Thomson et al., "The Potential of the Bulk Acoustic Wave Device as a Liquid-Phase Immunosensor", IEEE Transactions on Ultrasonics, Ferroelectrics and Frequency Control, volume USFC 34, NO. 2, March 1987, pp. 127–135.

All the known sensors for measuring concentrations of a substance in liquids and for determining the physical properties of liquids operating on the basis of piezoelectric resonators have in brief the following drawbacks:

The small oscillator quartz plates are glued or clamped in a holding means, which can impair the resonance behavior of the resonator itself due to mechanical tensions. Moreover, glued and clamped electric contacts on the surface of small oscillator quartz plates are not totally reliable, in particular, when employed for measuring concentrations of substances in liquids. Precautions must be taken in order to avoid short circuits. A stable and uniform quality of the contacting is not possible by this means.

In all the known cases, the piezoelectric resonators are provided with contact areas, which are to be connected to an electrical oscillation circuit and respectively to a measuring system for electrical contacting, on both its front side as well as on its back side. The integration of the piezoelectric resonator in a casing with respective electric contacting is difficult and time consuming. Good stable quality of the electric properties, in particular, when using a piezoelectric resonator in a holding means, which permits bringing the small oscillator plate into contact with a to-be-examined liquid on one side, is impossible.

Holding means of this type are also called flow-through cells, which are a unit, in which the already electrically contacted small oscillator quartz plate is connected to the connecting electrodes. Furthermore, defined supply and drain channels are provided via which the to-be-examined liquid can be selectively supplied to the piezoelectric resonator and drained again. Such a type of flow-through cell is shown, for instance in FIG. 4 in M. Thomson's article cited above.

For flow-through cells of this type, the user needs much time and manual skill in replacing the cell. In particular, in the field of biosensors, replacement often becomes necessary, because each different to-be-detected substance requires an especially prepared flow-through cell. The work involved in this replacing hinders wide commercial acceptance of piezoelectric resonators.

SUMMARY OF THE INVENTION

The object of the present invention is to further develop a piezoelectric resonator in such a manner that it can be electrically contacted reliably and without the risk of short circuiting as well as integrated in holding devices free of any mechanical tension. Moreover, the piezoelectric resonator is integratable in a sensor element in accordance with the invention which is designed for the determination of the concentration of a substance contained in a liquid or for the determination of the physical properties of a liquid without requiring complicated, expensive sealing measures in order to ensure reliable operation, in particular, concerning electric short circuiting. The sensor element is designed to be fabricated and, in particular, designed in such a manner that sealing measures are obviated. The sensor element should, in particular, also be part of a flow-through cell permitting easy replacement within a measuring system. In particular, the flow-through cell should be electrically contactable without requiring complicated construction or difficult handling and connectable fluid-tight to a possible liquid channel system.

The present invention is based on improving a piezoelectric resonator of plane design having an electrode area and at least one counter electrode area on the piezoelectric resonator surface in such a manner that a first side of the piezoelectric resonator provides only an electrode area which is electrically conductively connected to an electrode area on the second side of the piezoelectric resonator on which the counter electrode area is provided which is electrically insulated against the electrode area.

The piezoelectric resonator designed as small oscillator quartz plate is provided with an electrode in accordance with the invention and counter electrode arrangement which permits contacting the piezoelectric resonator only from one single side. The electrode area, which is provided only on one side and is extended upward over the edge of the small oscillator quartz plate to the opposite side so that electrical contact of the electrode area can occur from the opposite side. In addition, the opposite side of the small oscillator quartz plate is provided with at least one contact area for the counter electrode which is disposed electrically insulated from the electrode area.

Alternatively or in addition to the electrical contacting of the electrode area on the opposite side of the oscillator quartz plate extends over the edge of the small plate, the electric conduction paths can run perpendicular through the small plate and establish an electrical contact between the electrode areas on both surfaces of the small plate.

A central arrangement of a counter electrode area on the opposite side of the piezoelectric resonator is advantageous because reliable spacing between the electrode area to the counter electrode area located on the same side can be realized in this manner.

Alternatively or in addition, the intermediate spaces between the two electrically conducting areas are filled with electrically insulating material. Moreover, if needed, two or more counter electrode areas can be deposited on the resonator surfaces.

Suited as the material for the piezoelectric resonator is a a quartz shear oscillator, processed according to an AT cut.

In order to obtain sufficient adhesion between the small oscillator quartz plate and the to-be-deposited electrode and counter electrode layers, in addition, an adhesive layer is deposited directly on top of the surface of the small oscillator quartz plate, which preferably is composed of NiCr, Cr, Ni, Ti and/or W. Suited as the material for the electrode and the counter electrode area is preferably gold. The typical thickness of the adhesive layer ranges between approximately 10 to 50 nm, whereas the layer thickness of the electrode and counter electrode layers composed of electrically conductive material ranges between approximately 50 and 500 nm.

For electric contact of the piezoelectric resonator, the electrodes and counter electrodes deposited on the small oscillator quartz plate are provided with riblike steps intended for attaching connecting bonding wires. By providing concrete contact structures in the electrode and counter electrode areas, component specific deviations, which may effect eventual measuring results can be considerably limited.

The piezoelectric resonator of the invention is covered, as described in the preceding, with an electrode area which either extends from one side to the other side either over the edge of the resonator or via electric connecting channels to the other side of the resonator. A process in accordance with the invention the production of a coating of a small substrate plate is provided for economical production of piezoelectric resonators of this type comprising small plane substrate plates and preferably small oscillator quartz plates. This process comprises the following process steps:

Suited selected small substrate plates, purchasable in any desired size or thickness, are deposited on a carrier which fixes each small plate to at least one site of fixation in such a manner that the small plate is otherwise freely accessible for the coating procedure. A screening mask is placed on the small substrate plates deposited on the carrier. This screening mask is structured in such a manner that an area on the surface of the small plate that should not be coated is covered by a mask structure. Finally for fixation, a fixation lid is firmly placed in a detachable manner on the screening mask. The lid is structured identical to the carrier. This arrangement bearing the to-be-coated small substrate plates undergoes a known coating process in which both the upper side and the lower side of the small substrate plates are coated without needing to interrupt the process. In particular, the carrier structure of the invention ensures coating of the small plate over the edge area from one side to the other side so that on the small plate the deposits surrounding the small plate can be precipitated.

The coating procedure occurs in a usual manner using CVD or sputtering processes. For better adhesion of the electrically conducting the electrode areas and counter electrode areas on the small plates, first an adhesive layer, which preferably is composed of nickel chrome, nickel, titanium and/or wolfram, is applied to the small substrate plates. Following precipitation of a usually 10 to 50 nm thick adhesive layer, an electrically conductive layer, which for many applications of piezoelectric resonators is composed of gold and has a thickness of approximately 50–500 nm, is precipitated onto the adhesive layer. Depending on further use, passivation layers, composed of the following element compounds, $SiC$, $Fi_3N_4$, $SiO_2$, are precipitated onto the small substrate plates.

Depending on th e surface quality of the commercially available small substrate plates, prior to the coating procedure, the small substrate plates deposited in the carrier structure should undergo a cleaning step, which may be conducted as part of an as such known etching procedure. Of course, the materials of the carrier, the screening mask and the fixation lid should be selected in such a manner that they are inert to the to-be-conducted etching respectively coating procedure. Aluminum has proven to be a suited material for this purpose.

Fundamentally, the piezoelectric resonator of the invention can be versatilely employed, such as in telecommunication devices requiring a very stable resonance frequency. However, the following embodiments will focus on the use of a piezoelectric resonator as a sensor element, with which the concentration of substances dissolved in liquids can be detected and determined and the physical properties of liquids can be measured.

By means of the electrode arrangement of the invention on the piezoelectric resonator, a sensor element for determining the concentration of a substance contained in a liquid or for the determination of the physical properties of a liquid is designed in such a manner that the sensor element is electrically contactable solely on one single side and in this manner is connectable to a signal source and a measuring arrangement required for operating the sensor element.

Electrical contacting of the sensor element from only one side permits bringing the to-be-examined liquid into contact solely with the side of the piezoelectric resonator on which solely the electrode area is deposited. By changing its resonance behavior upon contacting the to-be-examined liquid, the sensor element is able to determine the physical properties of the fluid as to its viscosity, elasticity as well as density. If, in addition, a chemical a biochemical layer is deposited on the electrode area side onto which layer substances contained in a to-be-examined liquid are selectively precipitated are added, mass accumulates on this side by means of which the resonance behavior of the piezoelectric resonator is also influenced.

For operative conduction of the measures mentioned in the preceding, the sensor element of the invention is integrated in a flow-through cell designed according to the present invention, which is preferably designed as a disklike injection mold part and is provided according to the present invention with two electrical contact areas on its surface, which is connectable via connecting respectively bonding wires to the contact areas for the electrode and counter electrode of the sensor element. In order to integrate the sensor element in the injection mold part, the latter is provided with a recess on its surface, into which the sensor element is insertable. The sensor element encloses a hollow space with its side which is provided solely with the electrode area and the injection mold part. This hollow space forms the flow-through cell volume and is provided with at least two passage channels through which the to-be-examined fluid can be supplied respectively drained.

The particular advantage of the flow-through cell designed according to the present invention is that the flow-through cell can be easily implemented and removed again as an easily replaceable module in a measuring arrangement designed for measuring the concentration of a substance in a liquid respectively for determining the physical properties of a liquid. In particular, by simply contacting the sensor element by means of bonding wires, the flow-through cell ensures a tension-free seat not irritated by tensile stress which can, for example, act on the sensor element via the connecting wires.

The actual electrical contacting of the flow-through cell occurs via the contacting areas which are deposited on the injection mold part and on which the suitably designed connecting contacts can be applied.

As a modular unit, the invented flow-through cell is suited for uncomplicated and quick insertion in a measuring arrangement, designed for determining the concentration of a substance contained in a liquid and/or the determination of the physical properties of the liquid. As in all the known arrangements, the insertion of the sensor element and the flow-through cell enclosing the sensor element, involves great manual skill, particularly as often firm adhesive connection and complicated sealing measures are employed, a generic arrangement, as for instance described in DE 40 13 665 C2, is designed according to the present invention by being able to couple a liquid channel system in a liquid tight manner on the one side of the flow-through cell and connecting electrodes for a signal source and a measuring arrangement are connectable to the electric contacting areas on the opposite surface of the flow-through cell.

This arrangement is provided with a type of quick-change casing, composed of two casing parts which can be firmly fixed against each other, between which the flow-through cell has only to be placed in a corresponding indentation matching the outer contour of the flow-through cell. Further details on the arrangement according to the invention are described in connection with the figures.

The measuring arrangement composed of individual components of the invention described in the preceding is suited for conducting various measurements. Thus, using suited biochemical reaction layers, which can be deposited on one side of the piezoelectric resonator, permits determining the concentration of specific biochemical substances and microorganisms. This arrangement can quasi be considered as an immunosensor. The reaction kinetics between at least two substances can also be determined, with one substance being precipitated on the resonator surface in an immobilized form. Even without any additional depositing of a biochemically active layer on the surface of the piezoelectric resonator, the purpose of the arrangement of the invention is generally for measuring the physical properties of liquids. In particular, this arrangement can also be employed as a detergent sensor or a process rheometer.

BRIEF DESCRIPTION OF THE DRAWINGS

The present invention is made more apparent using preferred embodiments with reference to the drawings by way of example without the intention of limiting the overall inventive concept. Shown is in.

DESCRIPTION OF PREFERRED EMBODIMENTS AND INDUSTRIAL APPLICABILITY

Figure 1A:
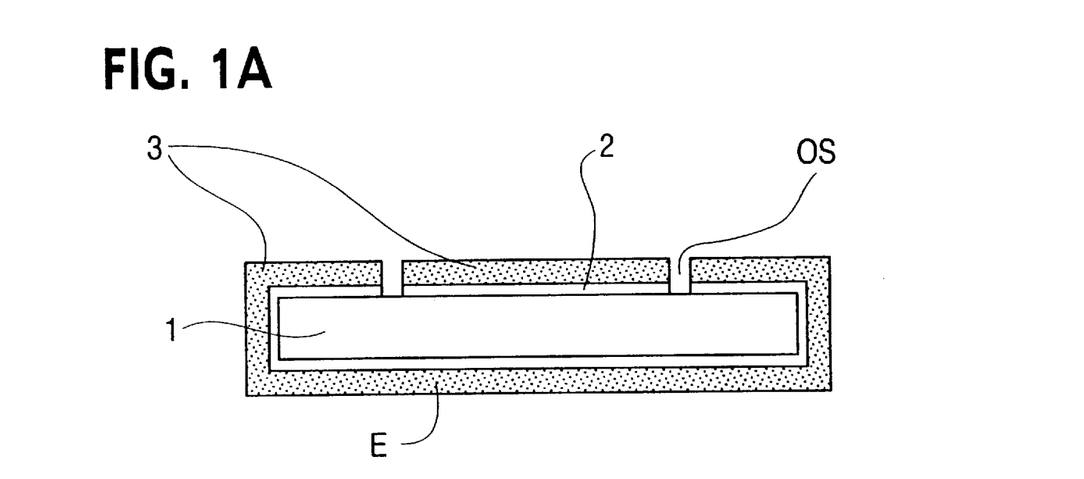
FIG. 1 is a cross section and top view of a piezoelectric resonator designed according to the present invention.
Figure 1B:
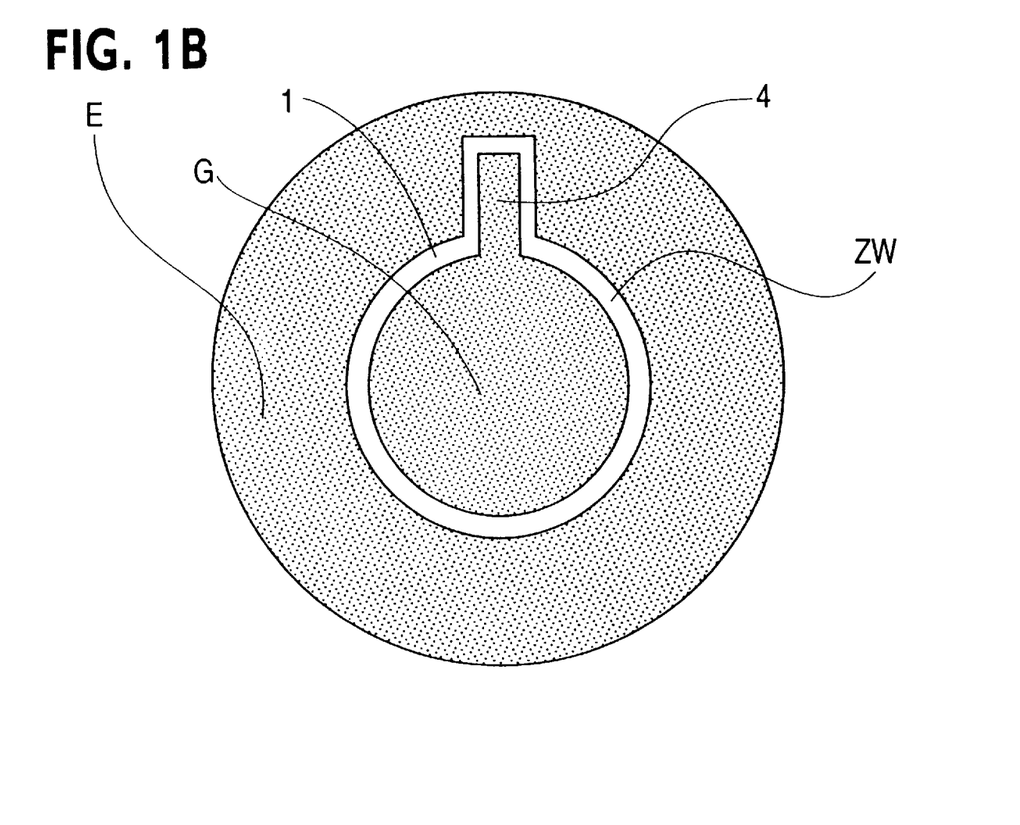

FIG. 1 shows in the upper part, a cross section of a coated piezoelectric resonator, whose core comprises a quartz substrate 1. According to FIG. 1 upper part, quartz substrate 1 designed as small oscillator quartz plate is nearly completely covered with an adhesive layer 2 with exception of the two let-open sites OS. Adhesive layer 2 comprises a titanium wolfram alloy and furthermore is coated with an electrically conductive layer 3, which preferably is of gold.

In the preferred embodiment according to FIG. 1, the entire lower side of the piezoelectric resonator is coated with a gold layer, which simultaneously also defines the electrode area E. Electrode area E extends over the edges of the piezoelectric resonator onto the upper side of the quartz substrate 1 on which, in addition, a counter electrode area G is precipitated, which is spaced a distance from electrode area E and thus is electrically insulated therefrom. An advantageous plane arrangement of electrode area E and counter electrode area G on the upper side of the piezoelectric resonator can be seen in the lower part of FIG. 1. In addition, the central counter electrode area G is provided with a riblike step 4 yielding an area for electrical contacting by means of bonding wires. In addition to the simple spatial distancing between the electrode area E and counter electrode area G, the intermediate space ZW can be filled with electrically insulating material in order to completely rule out short circuit effects, such as may occur for instance due to moisture.

Figure 2:
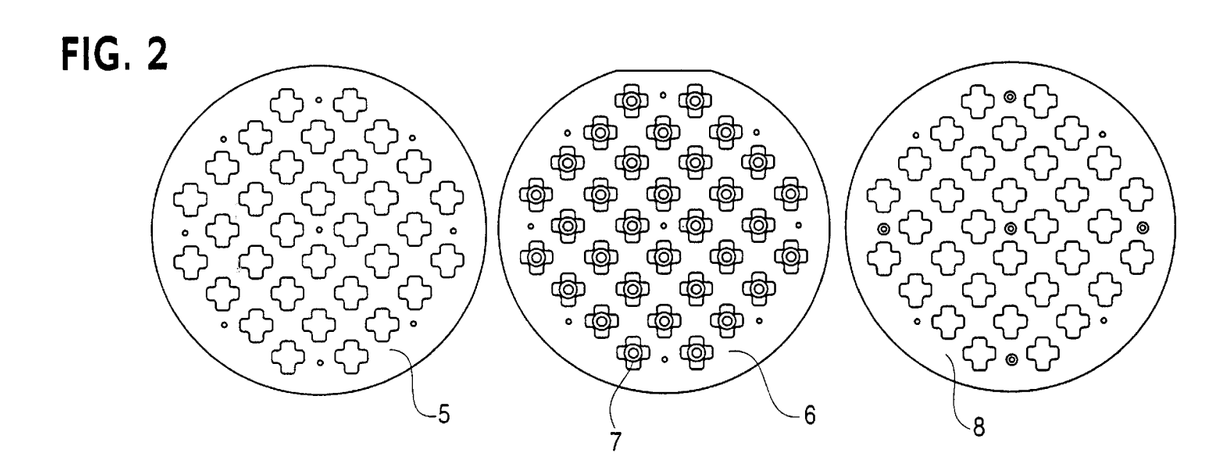
FIG. 2 is required carrier structures for conducting the process for fabricating the piezoelectric resonator shown in FIG. 1.

The piezoelectric resonator shown in FIG. 1 can be fabricated with the aid of the carrier structures shown in FIG. 2. Although a round small oscillator quartz plate is shown in FIG. 1, other geometric shapes, for example rectangular shapes, are also possible.

For coating, the untreated small oscillator quartz plates, which if need be undergo an etching step for cleaning, are deposited on a carrier 5 depicted in the top view on the left in FIG. 2. Carrier 5 is provided with a multiplicity of openings over which the to-be-coated small quartz plates are deposited. The openings are shaped in such a manner that the small plates lie on carrier 5 only with their edge area with minimal support area. In this manner it is ensured that the small plates are largely freely accessible for the materials precipitating on the small plates during the coating process.

A screening mask 6 is placed over the small quartz oscillator plates lying on carrier 5. This screening mask 6 provides one ring area 7 per to-be-coated small oscillator plate, which lies immediately on top of the small plate so that this particular area is not coated during a coating process. The purpose of a fixation lid 8 structured like carrier 5 is to fix screening mask 6.

The to-be-coated quartz substrates placed between the carrier structure can be coated on both sides with suitable layer material without opening the holding means without interrupting the coating process. In this way, first one adhesive layer is deposited on the individual substrate surfaces, in a first passage. Typically, the layer thickness is approximately 35 nm. Especially suited materials for this purpose are titanium wolfram alloys. Fundamentally any bondable metallizing layers are suited for precipitation of the electrically conductive material. However, as already mentioned in the preceding, in most cases gold is used.

Passivation layers, such as for example SiC, $Si_3N_4$, $SiO_2$ or plasma polymer layers, can also be deposited on the substrate surfaces in the same holding means.

Figure 3:
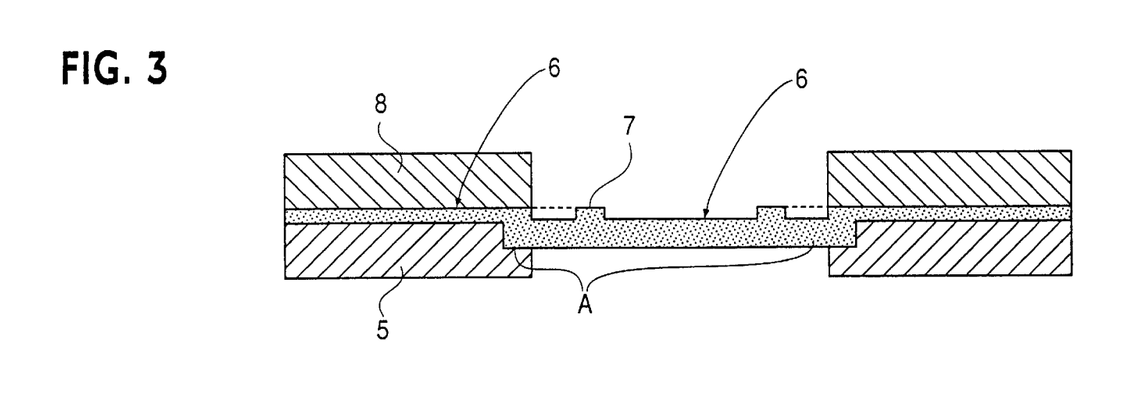
FIG. 3 is a longitudinal view of a section of the carrier structure for applying electrode material onto a piezoelectric resonator.

The masks shown in FIG. 2 are preferably made of aluminum and are provided with a mask diameter usually of 125 mm. FIG. 3 shows a cross section of a to-be-coated small oscillator quartz plate inserted between carrier 5 and fixation lid 7. Small oscillator quartz plate 1 projects for support only at the holding sites into approximately 100 $\mu$m deep steps A worked into carrier 5. Disposed immediately over the to-be-coated small oscillator quartz plate 1 and carrier 5 is screening mask 6 over which the fixation lid 7 is attached.

The fixation lid 7 is provided with connecting pins to carrier 5, via which the fixation lid can be fixed to carrier 5.

Due to the cross-shaped structure of the openings in carriers 5 and in fixation lid 8, the coating material can also reach the edges of the small oscillator plates so that the electrode area is contactable from one side onto the other side.

Figure 4:
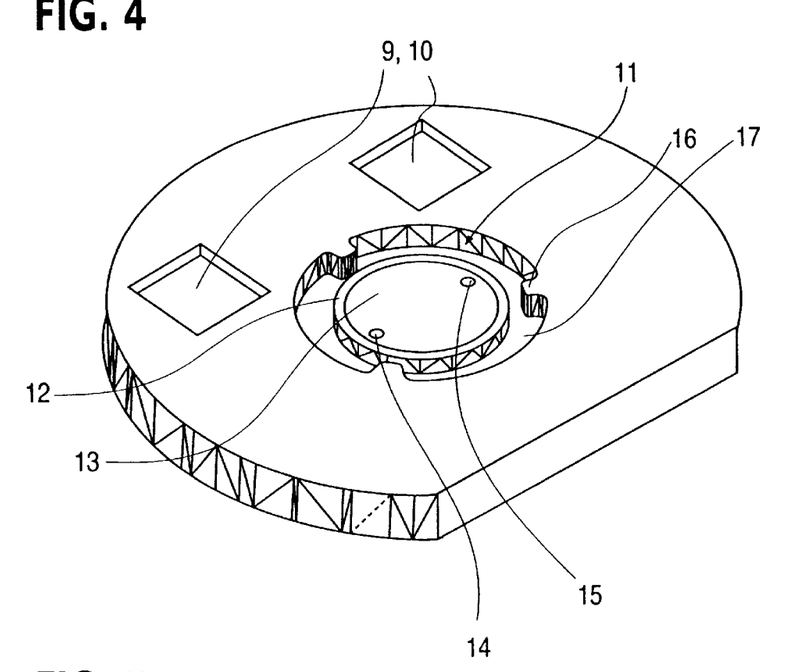
FIG. 4 is a exploded view of the basic structure of a flow-through cell.

FIG. 4 shows an injection mold part designed according to the present invention for realization of a flow-through cell which is made of plastic, for production and chemical stability reasons, preferably of polyarylether ketone. PEEK, in particular, offers in the case of thin layers, on the one hand, acceptable thermal junctions and, on the other hand, it is chemically stable, heat resistant up to 300° C. and easy to process.

On the surface of the molded body according to FIG. 4 produced by means of an injection mold process, two indentations 9, 10 are provided, into which the contact areas for electrical contacts, preferably small gold-sputtered silicon plates (not shown in the figure), can be glued.

An indentation 11 suited for placing the sensor element described in the preceding is worked into the center of the molded body. Worked into indentation 11 is a structure, which provides a encircling support rib 12, which projects ringlike over an internal surface 13 surrounded by support 12. Two passage channels 14 and 15, through which the to-be-examined liquid can be supplied or drained, are worked into internal surface 13. Flush on the support rib 12 is placed a small oscillator quartz plate, not shown in FIG. 4, which is centered in the indentation 11 on the support rib 12 by three guide boundaries 16. The sensor element lying on support rib 12 is firmly fixed by means of a suitable adhesive, with the excessive adhesive being able to run into groove 17 peripherally encircling support rib 12. In this embodiment, the sensor element encloses a hollow space between the bottom of the small oscillator quartz plate and internal surface 13. This hollow space forms the flow-through cell chamber. On the opposite upper side of the sensor element, the electrodes and counter electrodes are connected to electric contact surfaces 9 and 10 by means of bonding wires. Due to the relatively large surface design of the contact surfaces 9 and 10, the latter provide relatively robust electric connecting means designed as connecting electrodes which can be set on the contacting areas.

Independent of the mechanical press-on pressure of eventual connecting electrodes on the electric contacting areas 9 and 10, the electric contacting of the glued-on sensor elements remain free of external mechanical tensions, because the sensor element is solely contacted by means of the finest bonding wires.

The flow-through cell shown in FIG. 4 is to be considered a modular component and to be modified according to the desired measurement tasks. The flow-through cell permits quick attachment to and detachment from a measuring arrangement, which is described in the following and the cell can, furthermore, be understood as a commodity respectively as a disposable article.

Figure 5:
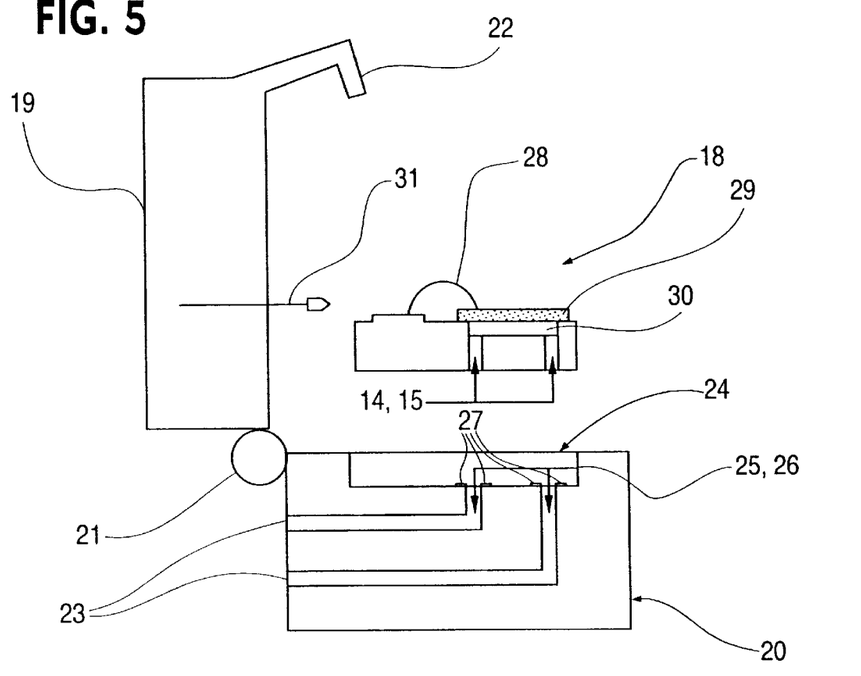
FIG. 5 is a schematic cross section representation of a quick-change casing designed according to the present invention and, FIG. 6 is an exploded view of a preferred embodiment of a quick-change casing.

FIG. 5 shows a preferred embodiment of a measuring arrangement for measuring the concentration of a substance contained in a liquid and/or determining the physical properties of the liquid. The arrangement comprises two casing parts 19, 20 which can be joined via a hinge 21 in a swinging manner. Moreover, the upper casing part 19 is provided with a locking hook 22 by means of which the upper casing part 20 and lower casing part can be firmly borne against each other. The lower casing part 20 is equipped with a liquid channel system 23 through which one channel can conduct the to-be-examined liquid to casing part 20 and the fluid can be drained via another channel out of the casing part.

Furthermore, the lower casing part is provided with a recess 24, which is shaped to fit the external contour of the flow-through cell bearing the reference number 18. Openings 25, 26 of the liquid channel system 23 are worked into lower casing part 20 flush with the passage channels 14, 15 worked into flow-through cell 18. For liquid tightness between the lower casing part 20 and the flow-though cell 18 seal rings 27 are provided respectively.

Flow-through cell 18 comprises, like in the just described case with reference to FIG. 4, an injection mold part into which two electric contact areas 9, 10 are worked which are electrically connected via bonding wires 28 to the electrodes respectively to the counter electrodes areas on sensor element 29. Sensor element 29 encloses with the flow-through cell a flow-through cell volume 30, in which the to-be-examined liquid comes into contact with the lower side of sensor element 29, which influences the resonance behavior of the sensor element.

Flow-through cell 18 placed into recess 24 is contacted by means of connecting electrodes 31 designed as spring contacts connected to upper casing part 19. By means of a suitable locking means of the two casing parts 19 and 20 using locking hook 22, the flow-through cell is pressed liquid tight from the top against seals 27 and simultaneously electrically contacted with the aid of spring contacts 31.

The measuring arrangement gains in attractiveness, in particular, by the fact that the flow-through cell can be reliably integrated in the system by means of simply swinging the two casing parts towards each other and locking them. Following completion of a measurement, the flow-through cell is replaced by removal from the measuring arrangement in a simple and cost-effective manner by implementing a new, unused flow-through cell. The measuring arrangement is designed quasi as a quick-change measuring casing, which permits a multiplicity of differently prepared flow-through cells in immediate measuring succession without great effort in exchanging them.

Figure 6:
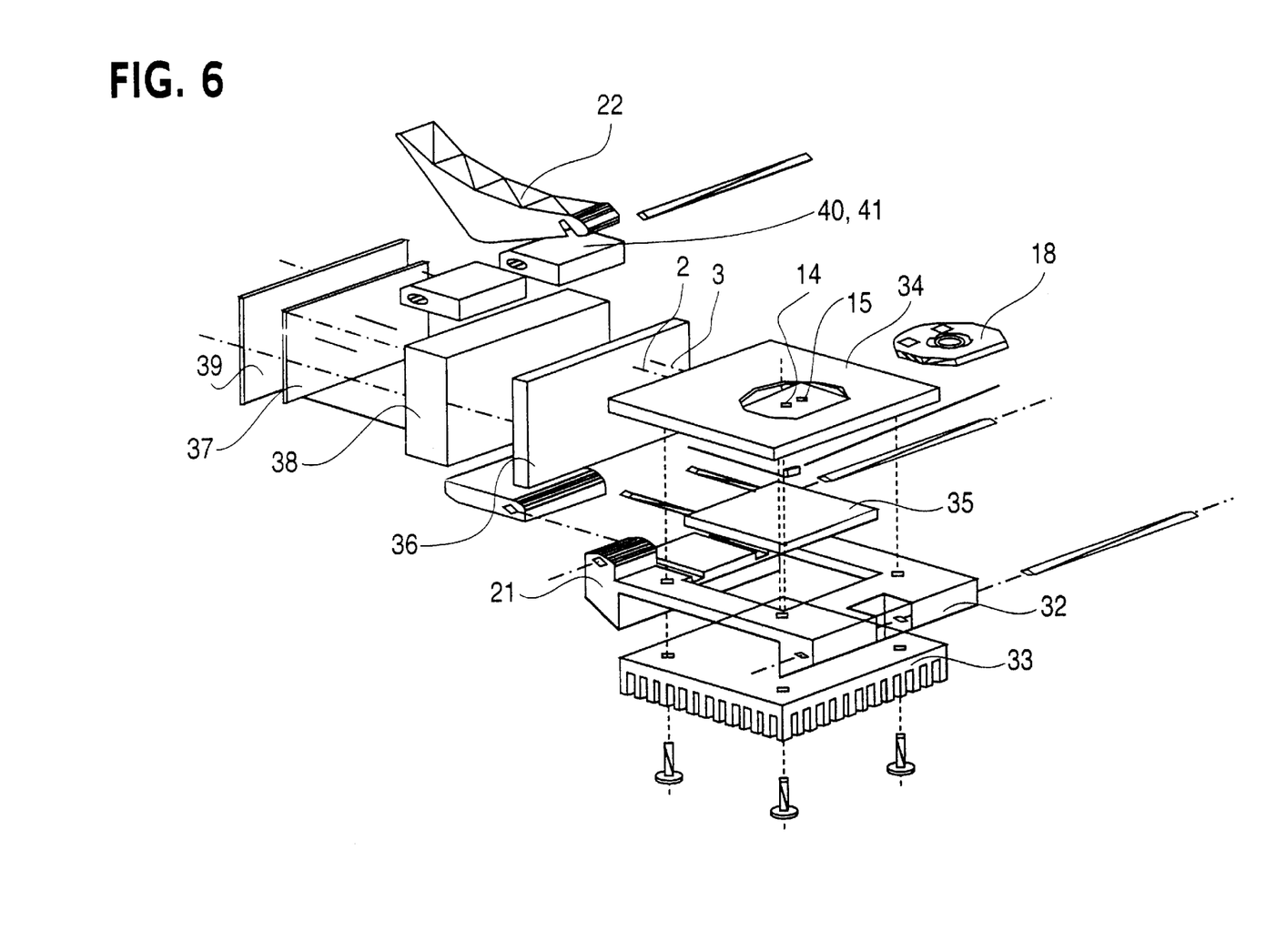

FIG. 6 shows a detailed view of the quick-change casing described in the preceding within the scope of an exploded view. The lower casing part 19 is composed of a multiplicity of single components: a carrier plate 32, to which hinge joint 21 is connected, has the purpose of receiving a cooling body 33 as well as a base plate 34. Moreover, carrier plate 32 possesses countersunk areas for the reception of a heating/cooling device 35, which preferably is designed as a Peltier element. Cooling body 23 and base plate 34 are screwed fast to each other and to heating/cooling device 35 lying between them by means of carrier plate 32. Base plate 34 possesses on its upper side a recess for the reception of flow-through cell 18 and an indentation for easier removal of flow-through cell 18 from base plate 34. The supply and draining lines of fluid channel system 23 are attached behind base plate 34 and end in passage channels 14 and 15, which are placed symmetrically in the flow-through cell.

The top casing part 19 comprises a pressure plate 36, an oscillator 37 serving as a signal source for the operation of the piezoelectric resonator with the respective casing 38, a lid 39, the locking hook 22 and the respective holding elements 40 and 41.

Moreover, the purpose of oscillator casing 38 is to receive pressure plate 36, which is attached from the bottom to the oscillator casing as well as to attach holding means 40 and 41.

In order to replace flow-through cell 18, the measurement arrangement is unfastened via locking hook 22 and upper casing part 19 is opened as far as possible. Then the suitably prepared flow-through cell is placed in the provided recess in the base plate preferably with the aid of a pair of tweezers. When closing the device, the flow-through cell is contacted via two spring contacts leading from the oscillator 37 through casing 38 and base plate 37. The liquid sealing of flow-through cell 18 against base plate 35 occurs by means of the pressure generated on seal rings 27 (see FIG. 5 in the base plate). In order to close the measuring arrangement, the locking hook 22 is pressed downward until it catches in a respective locking means.

The advantage of this setup is the ability to replace the flow-through cell quickly and its simple handling. The inflow opening in the base plate is so far from the actual measuring cell that drifting of the oscillator frequency due to thermal tension can be minimized. Moreover, the design of the measuring arrangement ensures that the to-be-examined liquid runs through a sufficiently long path through the base plate whose temperature is regulated by the heating and cooling device in order to balance the temperature required for stable measuring.

Depending on the preparation of the sensor element inserted in the flow-through cell, various measurement tasks can be fulfilled. If the sensor element is coated on one side with a biological substance preferably an antigen, selective microorganism or similar components of the to-be-examined liquid precipitate on the sensor surface. The changes in the mass on the resonator surface occurring thereby lead to a change in resonance which results in a change in the resonance frequency and/or in the oscillation amplitude. With the aid of a suited measurement arrangement, these changes in resonance can be precisely determined and put into relationship of the concentration of the substances deposited in the to-be-examined liquid respectively fluid. A preferred field of application of the measurement arrangement descried in the preceding is detection of legionellae in water.

Even without an especially provided coating of the sensor element with a chemical or biochemical layer, the measurement arrangement serves to determine the physical properties of liquids, such a for example the determination of the density, viscosity and/or elasticity of liquids. In this manner, for example detergent sensors or process rheometers can be realized.

List of Reference Numbers 1 quartz substrate
2 adhesive layer
3 electrically conducting layer
4 riblike step
5 carrier
6 screening mask
7 ring area
8 fixation lid
9 indentation for electric contact surfaces
10 indentation for electric contact surfaces
11 indentation
12 support rib
13 interior surface
14 passage channel
15 passage channel
16 guide boundary
17 groove
18 flow-through cell 19 upper part of the casing
20 lower part of the casing
21 hinge
22 locking hook
23 liquid channel system
24 recess
25 opening of the liquid channel system
26 opening of the liquid channel system
27 seal rings
28 bonding wires
29 sensor element
30 flow-through cell volume
31 spring contact
32 carrier plate
33 cooling body
34 basic plate
35 heating/cooling device
36 pressure plate
37 oscillator
38 oscillator casing
39 lid
40,41 holding elements
OS open sites
E electrode area
G counter-electrode area
ZW intermediate space
A step

What is claimed is:

1. A piezoelectric sensor element comprising:
a substrate having a first side, a second side opposed to the first side and a side wall;
an electrically conductive coating which functions as an electrode which is disposed on the first side, the side wall and a part of the second side;
at least one electrically conductive counter electrode disposed on part of the second side and electrically insulated from the electrode; and
a pair of electrical contacts which are respectively resistively connected to the electrodes solely on the second side for connection to a measuring device which senses a variation of oscillation frequency of a resonant circuit which is caused by a mass deposition from a liquid onto the electrode disposed on the first side.

2. A sensor element according to claim 1, wherein:
the liquid is contactable with said first side and resonance of the resonant circuit is altered by physical properties of said liquid and is detectable by said measuring device.

3. A sensor element according to claim 1, wherein:
said first side is coated with a chemical or biochemical layer and is contactable with said liquid and a selective reaction with a substance contained in said liquid involves a change in mass of said chemical or biochemical layer.

4. A flow through cell having a sensor element according to claim 1 wherein:
said flow through cell has a surface having two electric contact areas which are connectable to the pair of electrical contacts.

5. A flow through cell according to claim 4 wherein:
said flow-through cell has an indentation in a body on which said sensor element is positionable and in conjunction with said flow-through cell encloses a hollow space which is connected with at least two passage channels running through said flow-through cell, through which a liquid to be examined is suppliable or drainable.

6. A flow through cell according to claim 5, wherein:
said indentation is circular.

7. A flow through cell according to claim 4 wherein:
a encircling rib support, on which said sensor element is deposited, is in said surface.

8. A flow through cell according to claim 4, wherein:
at least two lateral guide boundaries are provided which center said sensor element on said surface.

9. A flow through cell according to claim 4, wherein:
said flow-through cell is a dislike molded part.

10. A flow through cell according to claim 4, wherein:
said pair of electrical contacts are deposited on said surface in two recesses in said flow-through cell.

11. A flow through cell according to claim 4, wherein:
said electrical contacts comprise gold-coated silicon plates.

12. A flow through cell according to claim 4, wherein:
said sensor element is adhered to said flow-through cell.

13. A flow through cell according to claim 7, wherein:
a furrow structure, which receives excess adhesive, is disposed about said encircling rib support in said flow-through cell.

14. A flow through cell according to claim 4, wherein:
said flow-through cell is plastic.

15. An arrangement for determining a concentration of a substance contained in a liquid and/or determining physical properties of said liquid using said flow-through cell according to claim 4, wherein:
said arrangement is connectable to a liquid channel system and which is connectable in a fluid tight manner on one side to connecting electrodes for a signal source and measuring device to said electrical contacts on the surface of said flow-through cell.

16. An arrangement according to claim 15, comprising:
a casing with two casing parts which are placeable against each other and between which said flow-through cell is placeable and to which the liquid channel system is provided in one casing part, and wherein said flow-through cell is insertable in said casing part provided with said liquid channel system in a replaceable manner so that a liquid-tight coupling of said liquid channel system to said passage channels of flow-through cell is provided with seals, and said other casing part is provided with the connecting electrodes which are placeable on said electrical contacts of said flow-through cell, and by placing both said casing parts against each other, said flow-through cell is fixable relative to said liquid channel system and to said connecting electrodes.

17. An arrangement according to claim 15, wherein:
said connecting electrodes are contacts.

18. An arrangement according to claim 15, wherein:
said casing part provided with said liquid channel system has a recess, in which said flow-through cell is placeable, and matches a contour of said flow-through cell.

19. An arrangement according to claim 18, wherein:
said casing part provided with said liquid channel system is thermally couplable to a temperature sensor and/or to a heating/cooling device.

20. An arrangement according to claim 19, wherein:
said heating/cooling device is a Peltier element.

21. An arrangement according to claim 19, wherein:
said liquid channel system is coupled thermally to said heating/cooling device.

22. An arrangement according to claim 18, wherein:
both casing parts are joined so as to swing about an axis.

23. An arrangement according to claim 18, wherein:
said other casing part has a pressure plate which presses the flow-through cell onto the liquid channel system and has the signal source and a locking device.

24. An arrangement according to claim 23, wherein:
said locking device has a locking hook having a hinge supporting both casing parts in a detachable manner.

25. A use of said arrangement according to claim 15 for determination of a concentration of biochemical substances.

26. A use of said arrangement according to claim 15 for measuring reaction kinetics between at least two substances, with one substance being immobilized at the surface of said sensor element.

27. A use of said arrangement according to claim 15 for measuring a density, viscosity and/or elasticity of a liquid to be examined.

28. A use according to claim 27, wherein:
physical properties of the liquid to be examined are determinable by only contacting said sensor element with said liquid to be examined as a result of an influence on the resonance of the resonant circuit.

29. A use according to claim 28 as a detergent sensor.

30. A use according to claim 29 as a process rheometer.

* * * * *